United States Patent
Sussman et al.

(10) Patent No.: US 6,589,201 B1
(45) Date of Patent: Jul. 8, 2003

(54) LIQUEFRACTURE HANDPIECE TIP

(75) Inventors: Glenn Sussman, Lake Forest, CA (US); Martin J. Padget, Huntington Beach, CA (US); Donald M. Cohen, Irvine, CA (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/525,196

(22) Filed: Mar. 14, 2000

Related U.S. Application Data

(63) Continuation-in-part of application No. 09/429,456, filed on Oct. 28, 1999, which is a continuation-in-part of application No. 09/090,433, filed on Jun. 4, 1998.

(51) Int. Cl.[7] ............................................. A61M 1/00
(52) U.S. Cl. ..................................................... 604/27
(58) Field of Search ......................... 604/27, 114, 35, 604/22, 19, 28, 30, 48, 500, 521, 43, 44, 113, 131, 151, 153, 289–291, 294, 246, 247

(56) References Cited

U.S. PATENT DOCUMENTS

| | | |
|---|---|---|
| 3,589,363 A | 6/1971 | Banko et al. |
| 3,606,878 A | 9/1971 | Kellog |
| 3,818,913 A | 6/1974 | Wallach |
| 3,930,505 A | 1/1976 | Wallach |
| 3,994,297 A | 11/1976 | Kopf |
| 4,024,866 A | 5/1977 | Wallach |
| 4,169,984 A | 10/1979 | Parisi |
| 4,223,676 A | 9/1980 | Wuchinich |
| 4,246,902 A | 1/1981 | Martinez |
| 4,493,694 A | 1/1985 | Wuchinich |
| 4,515,583 A | 5/1985 | Sorrich |
| 4,517,977 A | 5/1985 | Frost |
| 4,570,632 A | 2/1986 | Woods |
| 4,577,629 A | 3/1986 | Martinez |
| 4,589,414 A | 5/1986 | Yoshida et al. |
| 4,589,415 A | 5/1986 | Haaga |
| 4,609,368 A | 9/1986 | Dotson, Jr. |
| 4,634,419 A | 1/1987 | Kreizman et al. |
| 4,634,420 A | 1/1987 | Spinosa et al. |
| 4,662,869 A | 5/1987 | Wright |
| 4,674,502 A | 6/1987 | Imonti |
| 4,696,298 A | 9/1987 | Higgins et al. |
| 4,706,669 A | 11/1987 | Schlegel |
| 4,753,234 A | 6/1988 | Martinez |
| 4,869,715 A | 9/1989 | Sherburne |
| 4,909,249 A | 3/1990 | Akkas et al. |
| 4,911,161 A | 3/1990 | Schechter |
| 4,922,902 A | 5/1990 | Wuchinich et al. |
| 4,974,581 A | 12/1990 | Wiskell |
| 4,986,827 A | 1/1991 | Akkas et al. |
| 4,989,583 A | 2/1991 | Hood |

(List continued on next page.)

FOREIGN PATENT DOCUMENTS

WO    WO 96/24314    8/1996

*Primary Examiner*—Brian L. Casler
*Assistant Examiner*—Ann Y Lam
(74) *Attorney, Agent, or Firm*—Jeffrey S. Schira

(57) ABSTRACT

A surgical handpiece having two coaxial tubes or channels mounted within a body. The first tube is used for aspiration and is smaller in diameter than the second tube so as to create an annular passage between the first and second tube. The annular passage communicates with a pumping chamber formed between two electrodes. The pumping chamber works by boiling a small volume of the surgical fluid. As the fluid boils, it expands rapidly, thereby propelling the liquid downstream of the pumping chamber out of the annular passage. The distal end of the annular gap is sealed by sealing together the distal ends of the first and second tube and a plurality or orifices or ports may be formed near the seal. As the expanding gas is propelled down the annular gap, the gas/liquid stream is forced out of the distal orifices in a controlled and directed manner. The distal end of the first and second tubes may contain a bend.

4 Claims, 17 Drawing Sheets

U.S. PATENT DOCUMENTS

| | | |
|---|---|---|
| 4,989,588 A | 2/1991 | Kubota et al. |
| 5,019,035 A | 5/1991 | Missirlian et al. |
| 5,106,364 A | 4/1992 | Hayafuji et al. |
| 5,154,694 A | 10/1992 | Kelman |
| 5,226,910 A | 7/1993 | Kajiyama et al. |
| 5,250,065 A | 10/1993 | Clement et al. |
| 5,261,923 A | 11/1993 | Soares |
| 5,275,607 A | 1/1994 | Lo et al. |
| 5,284,472 A | 2/1994 | Sussman et al. |
| 5,285,795 A | 2/1994 | Ryan et al. |
| 5,322,504 A | 6/1994 | Doherty et al. |
| 5,359,996 A | 11/1994 | Hood |
| 5,423,330 A | 6/1995 | Lee |
| 5,547,473 A * | 8/1996 | Peyman .................. 604/27 |
| 5,562,692 A | 10/1996 | Bair |
| 5,591,184 A | 1/1997 | McDonnell |
| 5,616,120 A | 4/1997 | Andrew |
| 5,653,692 A | 8/1997 | Masterson et al. |
| 5,669,923 A | 9/1997 | Gordon |
| 5,674,226 A | 10/1997 | Doherty et al. |
| 5,766,194 A | 6/1998 | Smith |
| 5,800,408 A * | 9/1998 | Strauss et al. ............. 604/264 |
| 5,865,790 A | 2/1999 | Bair |
| 5,947,988 A | 9/1999 | Smith |
| 6,039,715 A | 3/2000 | Mackool |
| 6,139,571 A | 10/2000 | Fuller et al. ............... 607/105 |
| 6,146,380 A | 11/2000 | Racz et al. ................. 606/41 |

\* cited by examiner

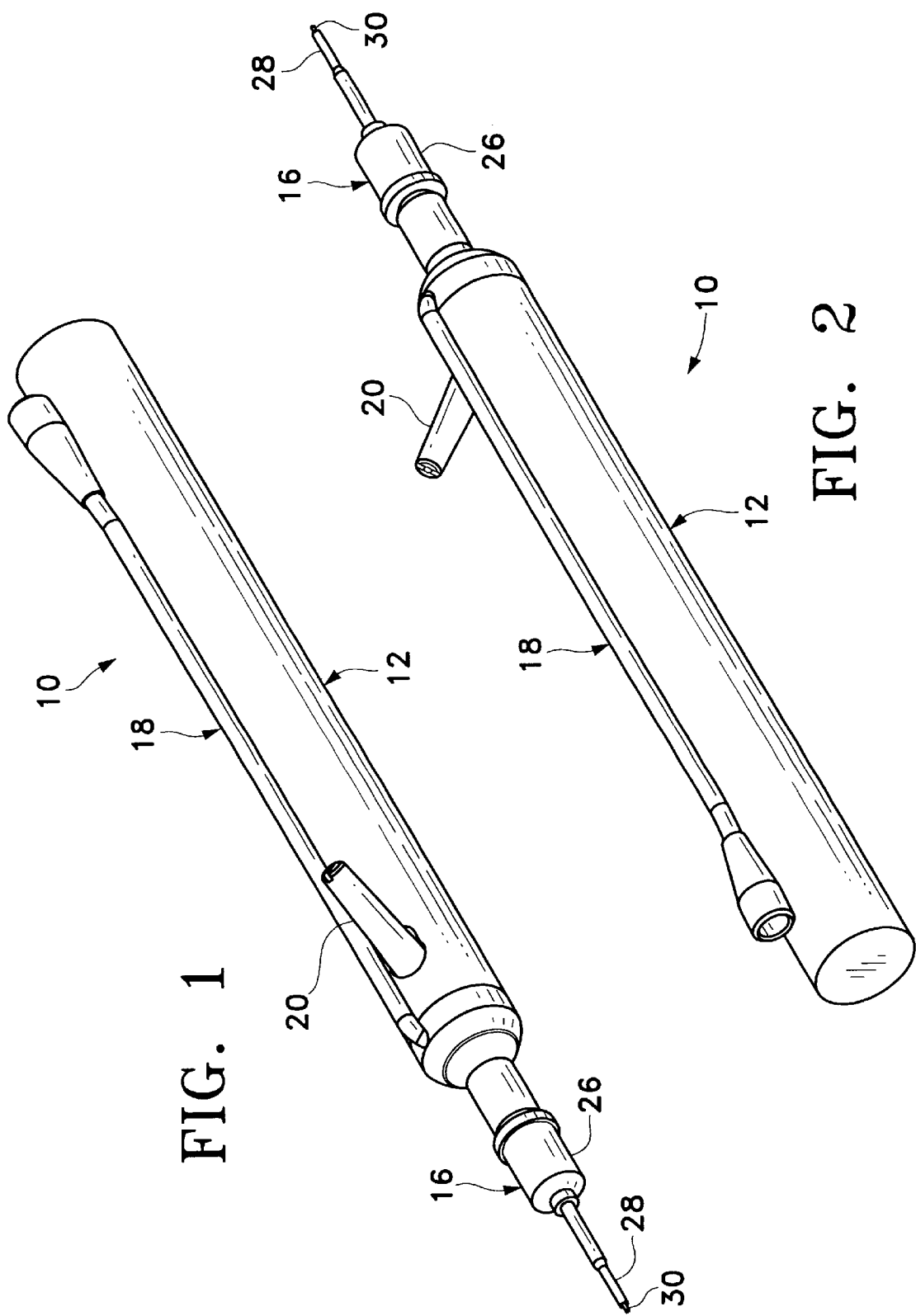

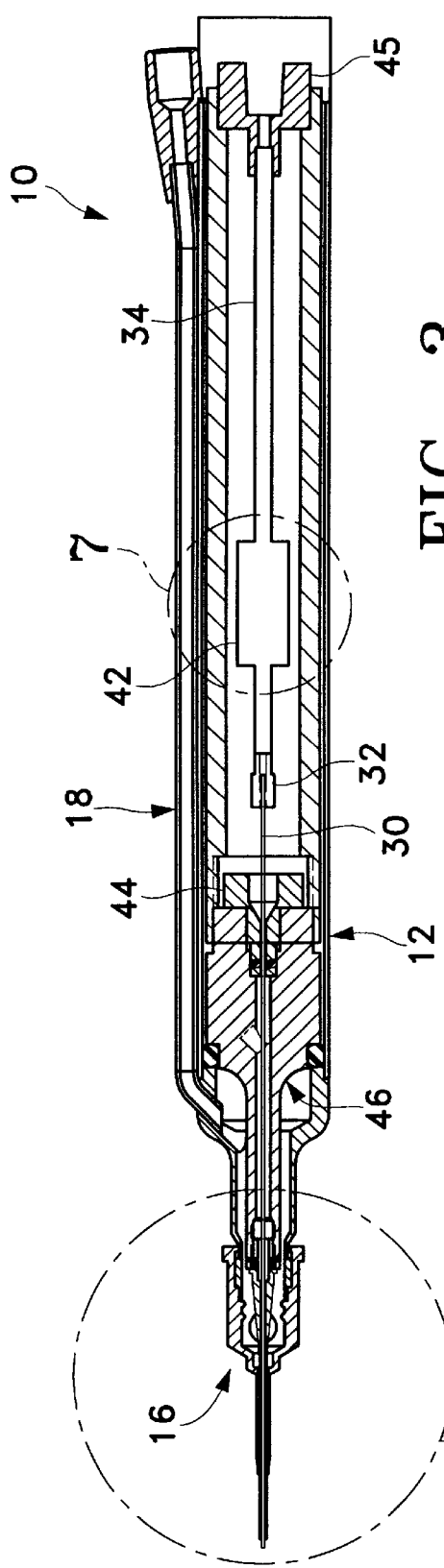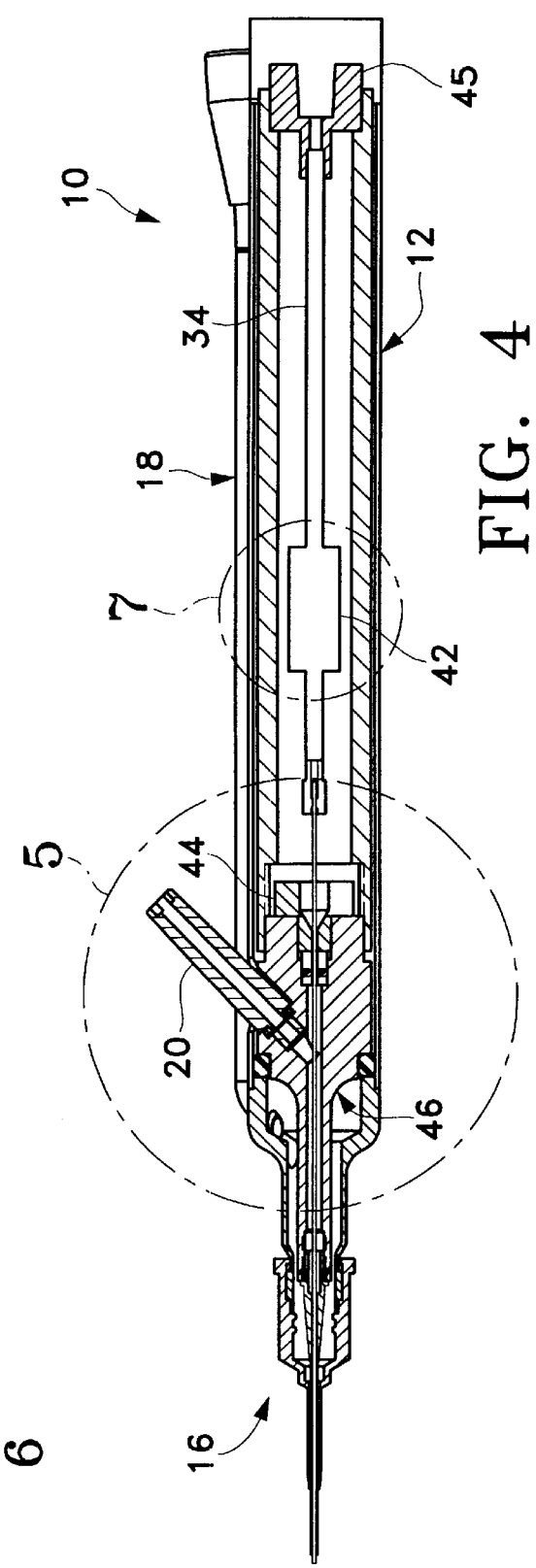

LIQUEFRACTURE HANDPIECE TIP

This application is a continuation-in-part application of U.S. patent application Ser. No. 09/429,456, filed Oct. 28, 1999, which is a continuation-in-part application of U.S. patent application Ser. No. 09/090,433, filed Jun. 4, 1998.

BACKGROUND OF THE INVENTION

This invention relates generally to the field of cataract surgery and more particularly to a handpiece tip for practicing the liquefracture technique of cataract removal.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubes. Through the electric cable, the console varies the power level transmitted by the handpiece to the attached cutting tip and the flexible tubes supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

Recently, a new cataract removal technique has been developed that involves the injection of hot (approximately 45° C. to 105° C.) water or saline to liquefy or gellate the hard lens nucleus, thereby making it possible to aspirate the liquefied lens from the eye. Aspiration is conducted concurrently with the injection of the heated solution and the injection of a relatively cool solution, thereby quickly cooling and removing the heated solution. This technique is more fully described in U.S. Pat. No. 5,616,120 (Andrew, et al.), the entire content of which is incorporated herein by reference. The apparatus disclosed in the publication, however, heats the solution separately from the surgical handpiece. Temperature control of the heated solution can be difficult because the fluid tubes feeding the handpiece typically are up to two meters long, and the heated solution can cool considerably as it travels down the length of the tube.

U.S. Pat. No. 5,885,243 (Capetan, et al.) discloses a handpiece having a separate pumping mechanism and resistive heating element. Such a structure adds unnecessary complexity to the handpiece.

Therefore, a need continues to exist for a simple surgical handpiece and tip that can heat internally the solution used to perform the liquefracture technique.

BRIEF DESCRIPTION OF THE INVENTION

The present invention improves upon the prior art by providing a surgical handpiece having two coaxially mounted tubes or channels mounted to a body. The first tube is used for aspiration and is smaller in diameter than the second tube so as to create an annular passage between the first and second tube. The annular gap communicates with a pumping chamber formed between two electrodes. The pumping chamber works by boiling a small volume of the surgical fluid. As the fluid boils, it expands rapidly, thereby propelling the liquid downstream of the pumping chamber out of the annular gap. The distal end of the annular gap is sealed by sealing together the distal ends of the first and second tube and a plurality or orifices or ports may be formed near the seal. As the expanding gas is propelled down the annular gap, the gas/liquid stream is forced out of the distal ports in a controlled and directed manner. The distal end of the first and second tubes may contain a bend.

Accordingly, one objective of the present invention is to provide a surgical handpiece having at least two coaxial tubes.

Another objective of the present invention is to provide a handpiece having a pumping chamber.

Another objective of the present invention is to provide a surgical handpiece having a device for delivering the surgical fluid through the handpiece in pulses.

Still another objective of the present invention is to provide a handpiece having a pumping chamber formed by two electrodes.

Yet another objective of the present invention is to provide a handpiece having two electrodes wherein the electrodes are insulated.

Still another objective of the present invention is to provide a handpiece that delivers fluid pulses in a controlled and directed manner.

These and other advantages and objectives of the present invention will become apparent from the detailed description and claims that follow.

BRIEF DESCRIPTION OF THE DRAWINGS

FIG. 1 is a front, upper left perspective view of a first embodiment of the handpiece of the present invention.

FIG. 2 is a rear, upper right perspective view of a first embodiment of the handpiece of the present invention.

FIG. 3 is a cross-sectional view of a first embodiment of the handpiece of the present invention taken along a plane passing through the irrigation channel.

FIG. 4 is a cross-sectional view of a first embodiment of the handpiece of the present invention taken along a plane passing through the aspiration channel.

DETAILED DESCRIPTION OF THE INVENTION

Figure 6:
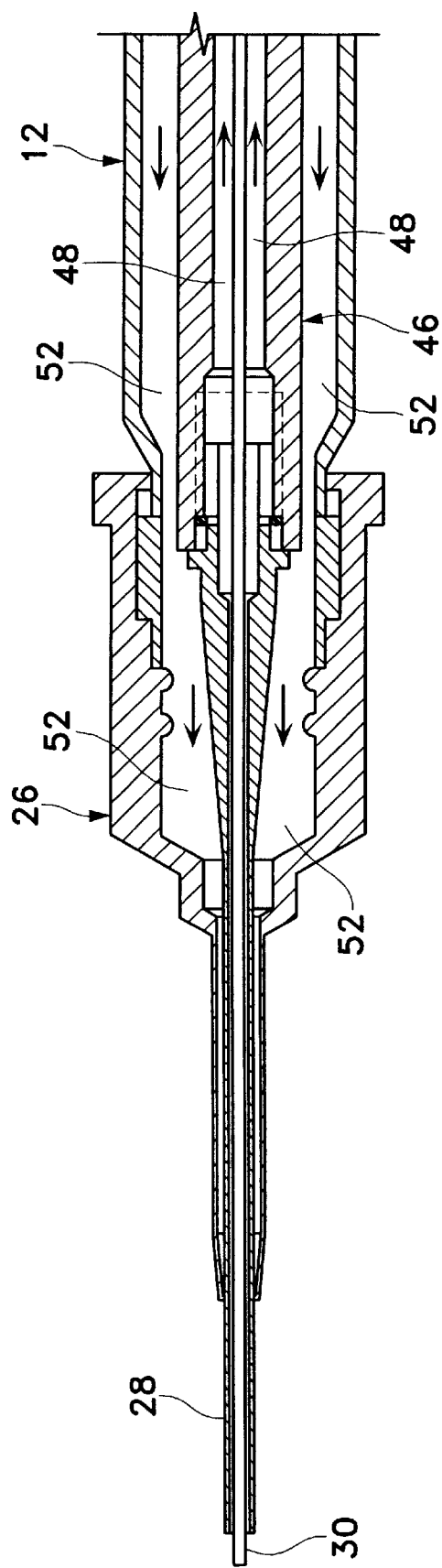
FIG. 6 is an enlarged partial cross-sectional view of a first embodiment of the handpiece of the present invention taken at circle 6 in FIG. 3.

Handpiece 10 of the present invention generally includes handpiece body 12 and operative tip 16. Body 12 generally includes external irrigation tube 18 and aspiration fitting 20. Body 12 is similar in construction to well-known in the art phacoemulsification handpieces and may be made from plastic, titanium or stainless steel. As best seen in FIG. 6, operative tip 16 includes tip/cap sleeve 26, needle 28 and tube 30. Sleeve 26 may be any suitable commercially available phacoemulsification tip/cap sleeve or sleeve 26 may be incorporated into other tubes as a multi-lumen tube. Needle 28 may be any commercially available hollow phacoemulsification cutting tip, such as the TURBOSONICS tip available from Alcon Laboratories, Inc., Fort Worth, Tex. Tube 30 may be any suitably sized tube to fit within needle 28, for example 29 gauge hypodermic needle tubing.

Figure 5:
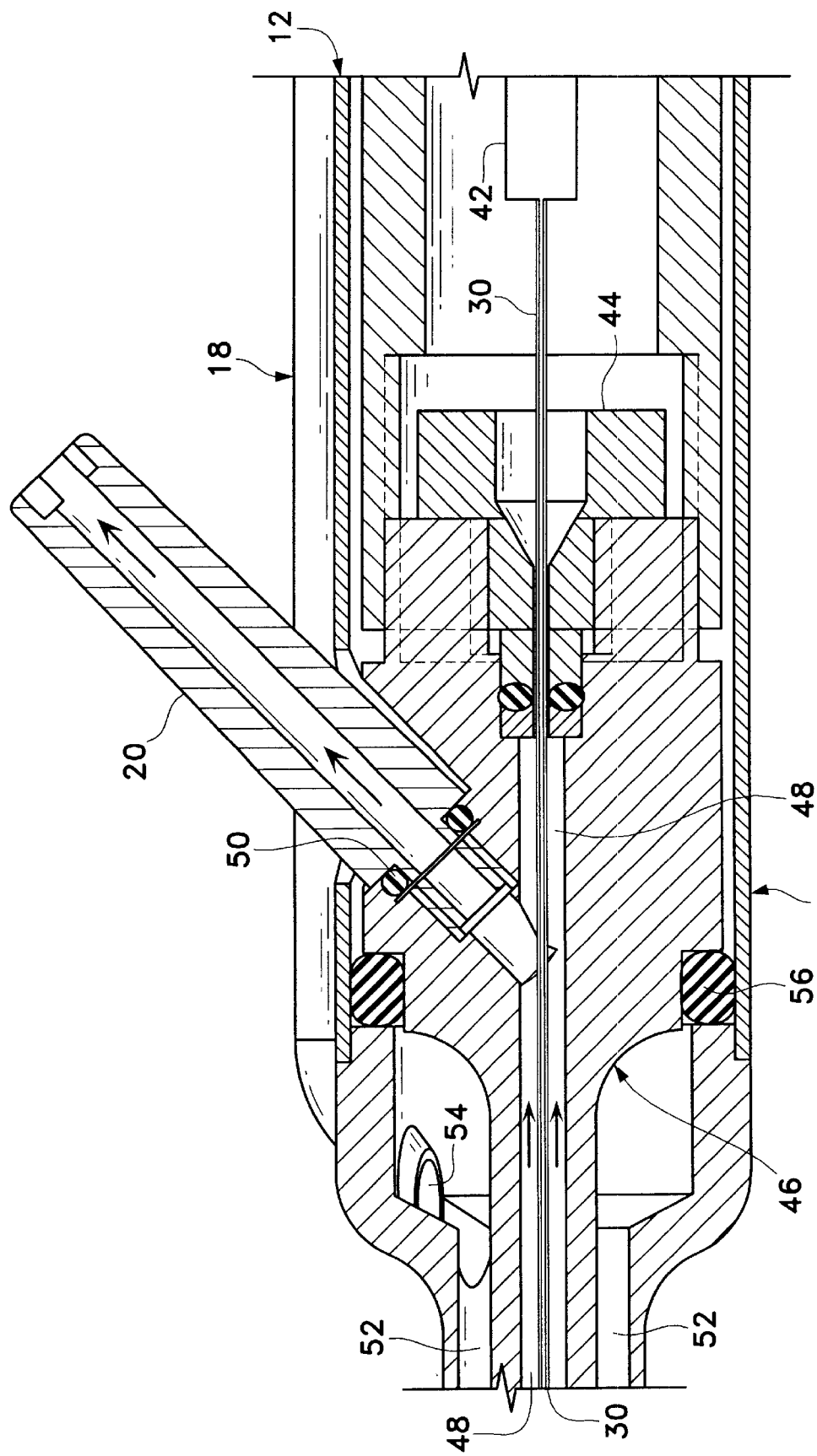
FIG. 5 is an enlarged partial cross-sectional view of a first embodiment of the handpiece of the present invention taken at circle 5 in FIG. 4.

As best seen in FIG. 5, tube 30 is free on the distal end and connected to boiling or pumping chamber 42 on the proximal end. Tube 30 and pumping chamber 42 may be sealed fluid tight by any suitable means having a relatively high melting point, such as a silicone gasket, glass frit or silver solder. Fitting 44 holds tube 30 within bore 48 of aspiration horn 46. Bore 48 communicates with fitting 20, which is journaled into horn 46 and sealed with O-ring seal 50 to form an aspiration pathway through horn 46 and out fitting 20. Horn 46 is held within body 12 by O-ring seal 56 to form irrigation tube 52 which communicates with irrigation tube 18 at port 54.

Figure 7:
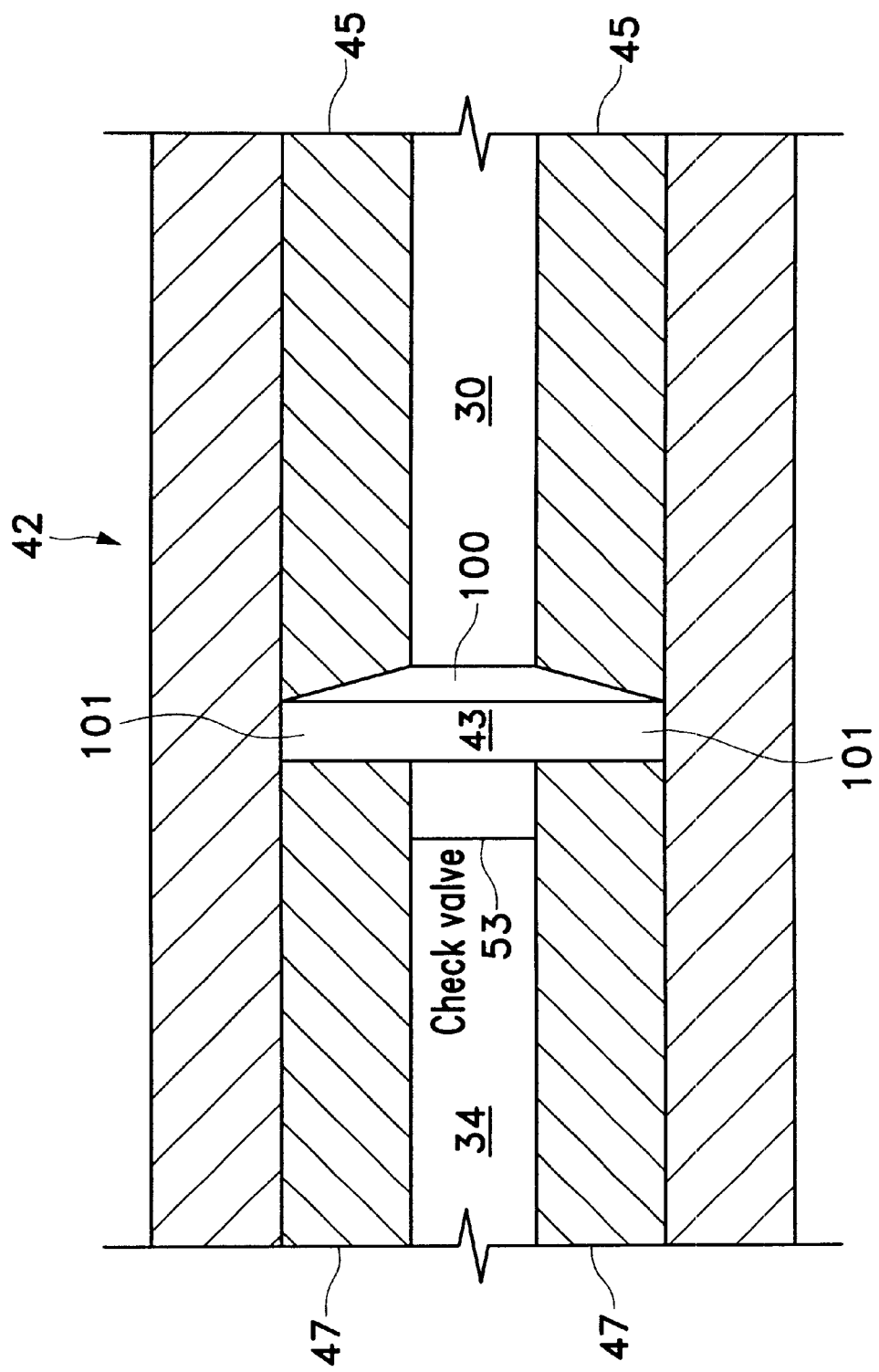
FIG. 7 is an enlarged cross-sectional view of a first embodiment of the handpiece of the present invention taken at circle 7 in FIGS. 3 and 4.

As best seen in FIG. 7, in a first embodiment of the present invention, pumping chamber 42 contains a relatively large pumping reservoir 43 that is sealed on both ends by electrodes 45 and 47. Electrical power is supplied to electrodes 45 and 47 by insulated wires, not shown. In use, surgical fluid (e.g. saline irrigating solution) enters reservoir 43 through tube 34 and check valve 53, check valves 53 being well-known in the art. Electrical current (preferably Radio Frequency Alternating Current or RFAC) is delivered to and across electrodes 45 and 47 because of the conductive nature of the surgical fluid. As the current flows through the surgical fluid, the surgical fluid boils. As the surgical fluid boils, it expands rapidly out of pumping chamber 42 through tube 30 (check valve 53 prevents the expanding fluid from entering tube 34). The expanding gas bubble pushes the surgical fluid in tube 30 downstream of pumping chamber 42 forward. Subsequent pulses of electrical current form sequential gas bubbles that move surgical fluid down tube 30. The size and pressure of the fluid pulse obtained by pumping chamber 42 can be varied by varying the length, timing and/or power of the electrical pulse sent to electrodes 45 and 47 and by varying the dimensions of reservoir 43. In addition, the surgical fluid may be preheated prior to entering pumping chamber 42. Preheating the surgical fluid will decrease the power required by pumping chamber 42 and/or increase the speed at which pressure pulses can be generated.

Figure 8:
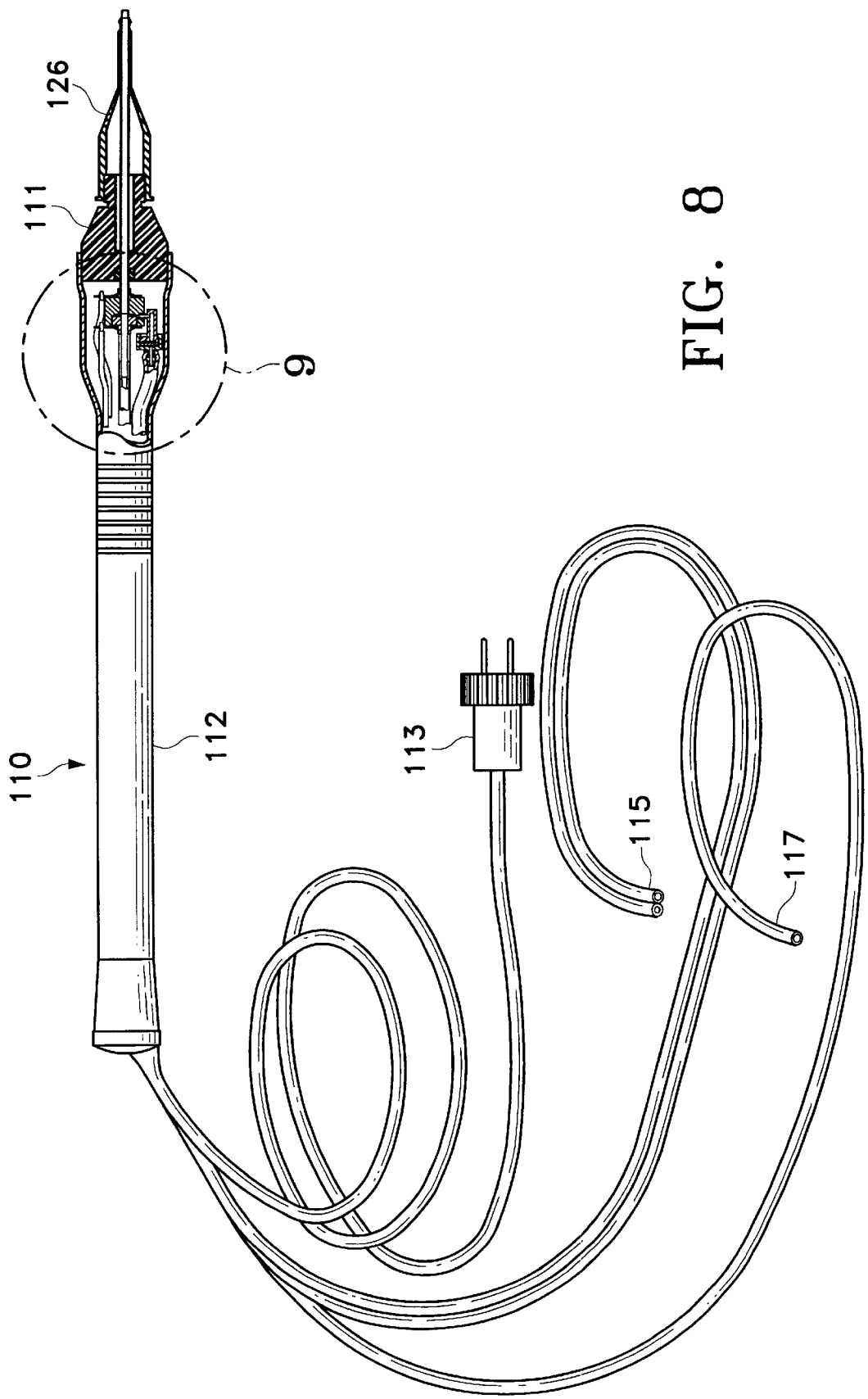
FIG. 8 is a partial cross-sectional view of a second embodiment of the handpiece of the present invention.
Figure 9:
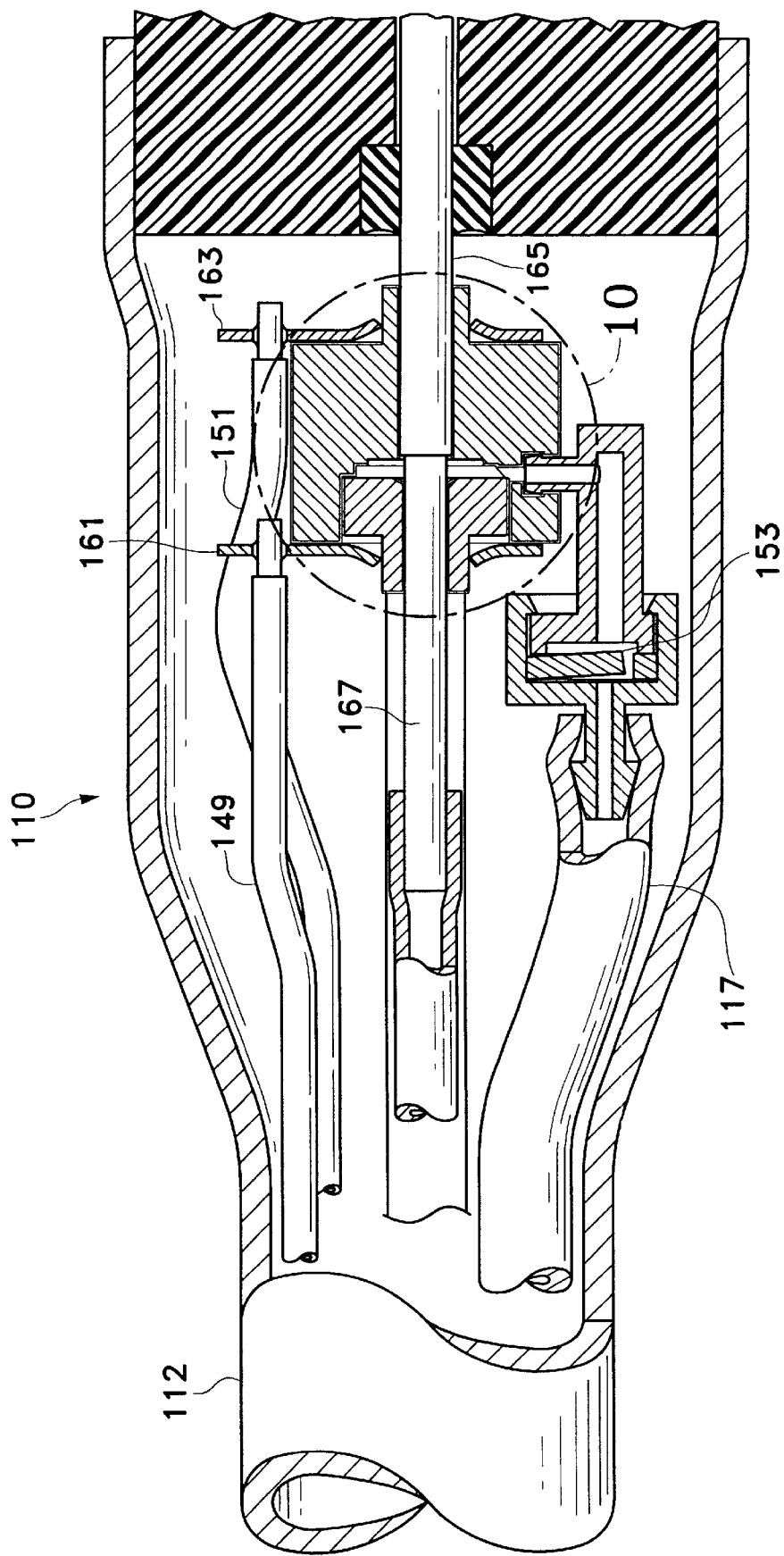
FIG. 9 is an enlarged partial cross-sectional view of the second embodiment of the handpiece of the present invention taken at circle 9 in FIG. 8.
Figure 10:
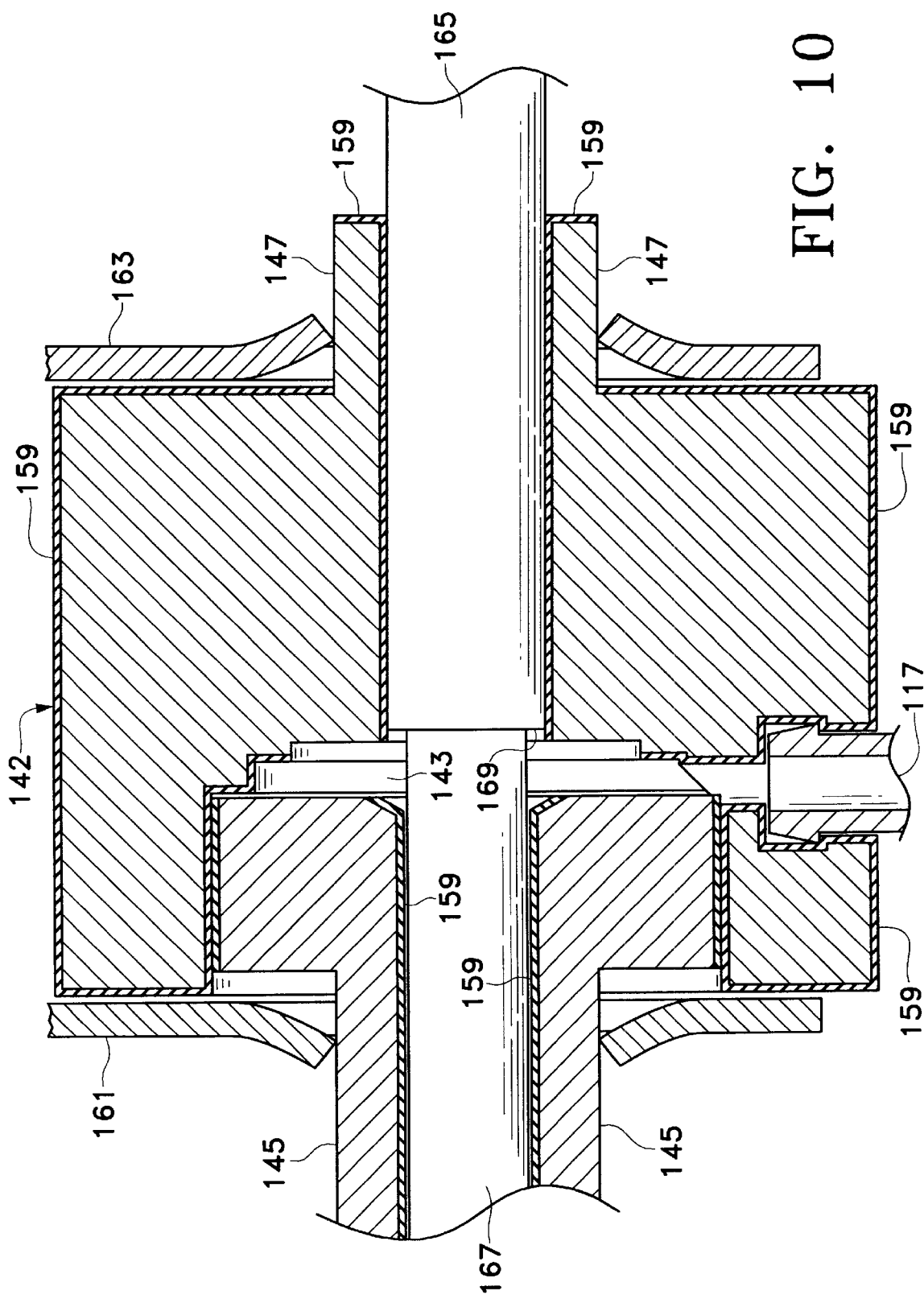
FIG. 10 is an enlarged partial cross-sectional view of the pumping chamber used in the second embodiment of the handpiece of the present invention taken at circle 10 in FIG. 9.

As best seen in FIGS. 8–10, in a second embodiment of the present invention, handpiece 110 generally includes body 112, having power supply cable 113, irrigation/aspiration lines 115, pumping chamber supply line 117. Distal end 111 of handpiece 110 contains pumping chamber 142 having a reservoir 143 formed between electrodes 145 and 147. Electrodes 145 and 147 are preferably made from aluminum, titanium, carbon or other similarly conductive materials and are electrically insulated from each other and body 112 by insulating layer 159 such as anodized layer 159 formed on electrodes 145 and 147. Anodized layer 159 is less conductive than untreated aluminum and thus, acts as an electrical insulator. Electrodes 145 and 147 and electrical terminals 161 and 163 are not anodized and thus, are electrically conductive. Layer 159 may be formed by any suitable insulating or anodization technique, well-known in the art, and electrodes 145 and 147 and electrical terminals 161 and 163 may be masked during anodization or machined after anodization to expose bare aluminum. Electrical power is supplied to electrodes 145 and 147 through terminals 161 and 163 and wires 149 and 151, respectively. Fluid is supplied to reservoir 143 through supply line 117 and check valve 153. Extending distally from pumping chamber 142 is outer tube 165 that coaxially surrounds aspiration or inner tube 167. Tubes 165 and 167 may be of similar construction as tube 30. Tube 167 is of slightly smaller diameter than tube 165, thereby forming an annular passage or gap 169 between tube 165 and tube 167. Annular gap 169 fluidly communicates with reservoir 143.

In use, surgical fluid enters reservoir 143 through supply line 117 and check valve 153. Electrical current is delivered to and across electrodes 145 and 147 because of the conductive nature of the surgical fluid. As the current flows through the surgical fluid, the surgical fluid boils. As the surgical fluid boils, it expands rapidly out of pumping chamber 142 through annular gap 169. The expanding gas bubble pushes forward the surgical fluid in annular gap 169 downstream of pumping chamber 142. Subsequent pulses of electrical current form sequential gas bubbles that move or propel the surgical fluid down annular gap 169.

One skilled in the art will recognize that the numbering in FIGS. 8–10 is identical to the numbering in FIGS. 1–7 except for the addition of "100" in FIGS. 8–10.

Figure 11:
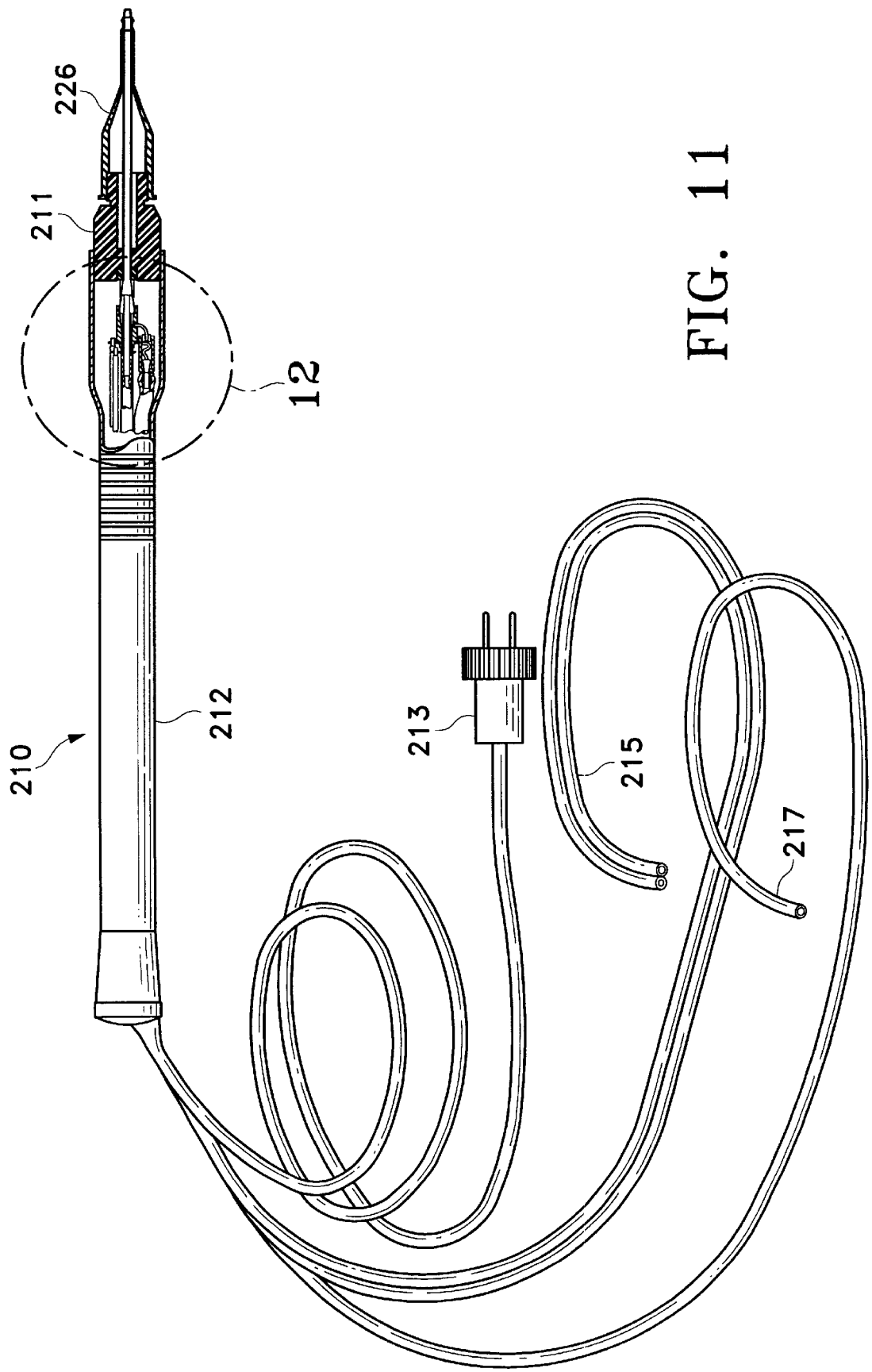
FIG. 11 is a partial cross-sectional view of a third embodiment of the handpiece of the present invention.
Figure 12:
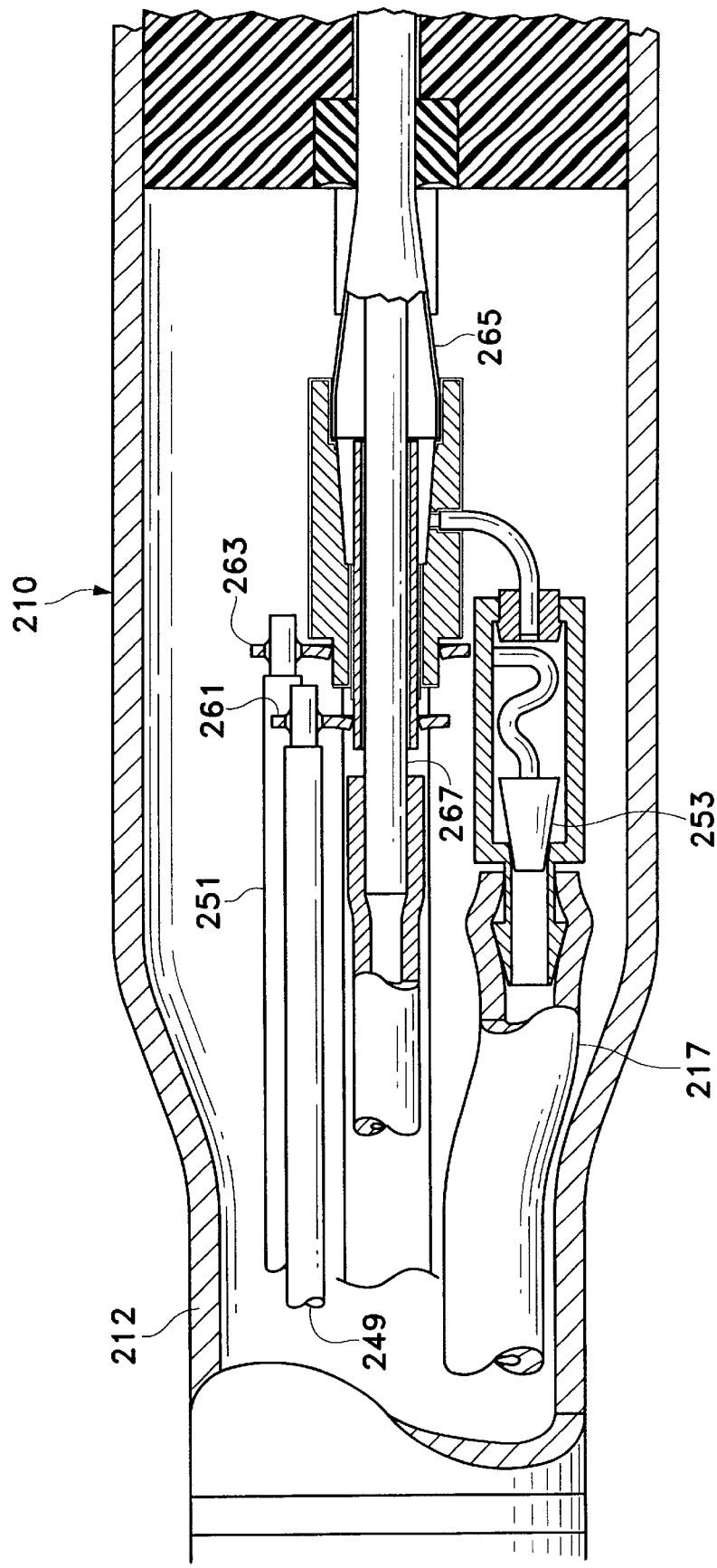
FIG. 12 is an enlarged partial cross-sectional view of the distal end of the third embodiment of the handpiece of the present invention taken at circle 12 in FIG. 11.
Figure 13:
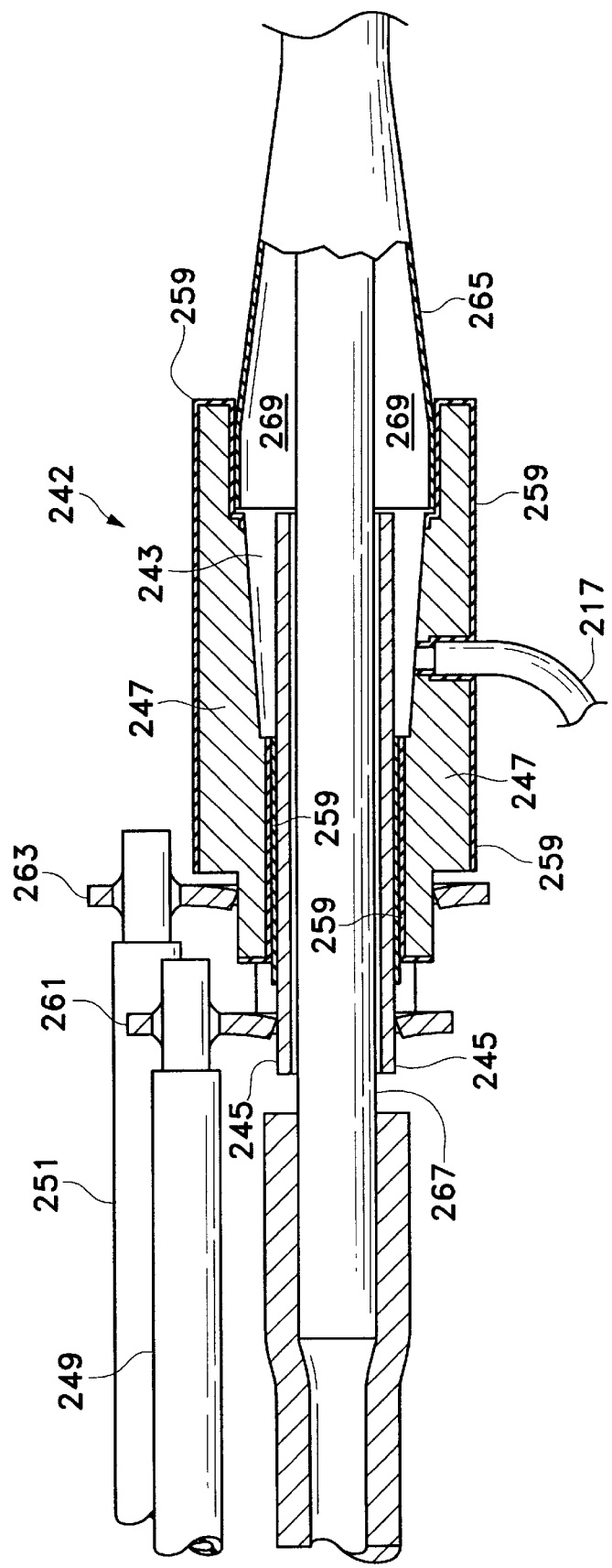
FIG. 13 is an enlarged partial cross-sectional view of the pumping chamber used in the third embodiment of the handpiece of the present invention shown in FIGS. 11 and 12.

As best seen in FIGS. 11–13, in a third embodiment of the present invention, handpiece 210 generally includes body 212, having power supply cable 213, irrigation/aspiration lines 215, pumping chamber supply line 217. Distal end 211 of handpiece 210 contains pumping chamber 242 having a reservoir 243 formed between electrodes 245 and 247. Electrodes 245 and 247 are preferably made from aluminum and electrically insulated from each other and body 212 by anodized layer 259 formed on electrodes 245 and 247. Anodized layer 259 is less conductive than untreated aluminum and thus, acts as an electrical insulator. Electrodes 245 and 247 and electrical terminals 261 and 263 are not anodized and thus, are electrically conductive. Layer 259 may be formed by any suitable anodization technique, well-known in the art, and electrodes 245 and 247 and electrical terminals 261 and 263 may be masked during anodization or machined after anodization to expose bare aluminum. Electrical power is supplied to electrodes 245 and 247 through terminals 261 and 263 and wires 249 and 251, respectively. Fluid is supplied to reservoir 243 though supply line 217 and check valve 253. Extending distally from pumping chamber 242 is outer tube 265 that coaxially surrounds aspiration or inner tube 267. Tubes 265 and 267 may be of similar construction as tube 30. Tube 267 is of slightly smaller diameter than tube 265, thereby forming an annular passage or gap 269 between tube 265 and tube 267. Annular gap 269 fluidly communicates with reservoir 243.

In use, surgical fluid enters reservoir 243 through supply line 217 and check valve 253. Electrical current is delivered to and across electrodes 245 and 247 because of the conductive nature of the surgical fluid. As the current flows through the surgical fluid, the surgical fluid boils. The current flow progresses from the smaller electrode gap section to the larger electrode gap section, i.e., from the region of lowest electrical resistance to the region of higher electrical resistance. The boiling wavefront also progresses from the smaller to the larger end of electrode 247. As the surgical fluid boils, it expands rapidly out of pumping chamber 242 through annular gap 269. The expanding gas bubble pushes forward the surgical fluid in annular gap 269 downstream of pumping chamber 242. Subsequent pulses of electrical current form sequential gas bubbles that move or propel the surgical fluid down annular gap 269.

One skilled in the art will recognize that the numbering in FIGS. 11–13 is identical to the numbering in FIGS. 1–7 except for the addition of "200" in FIGS. 11–13.

Figure 14:
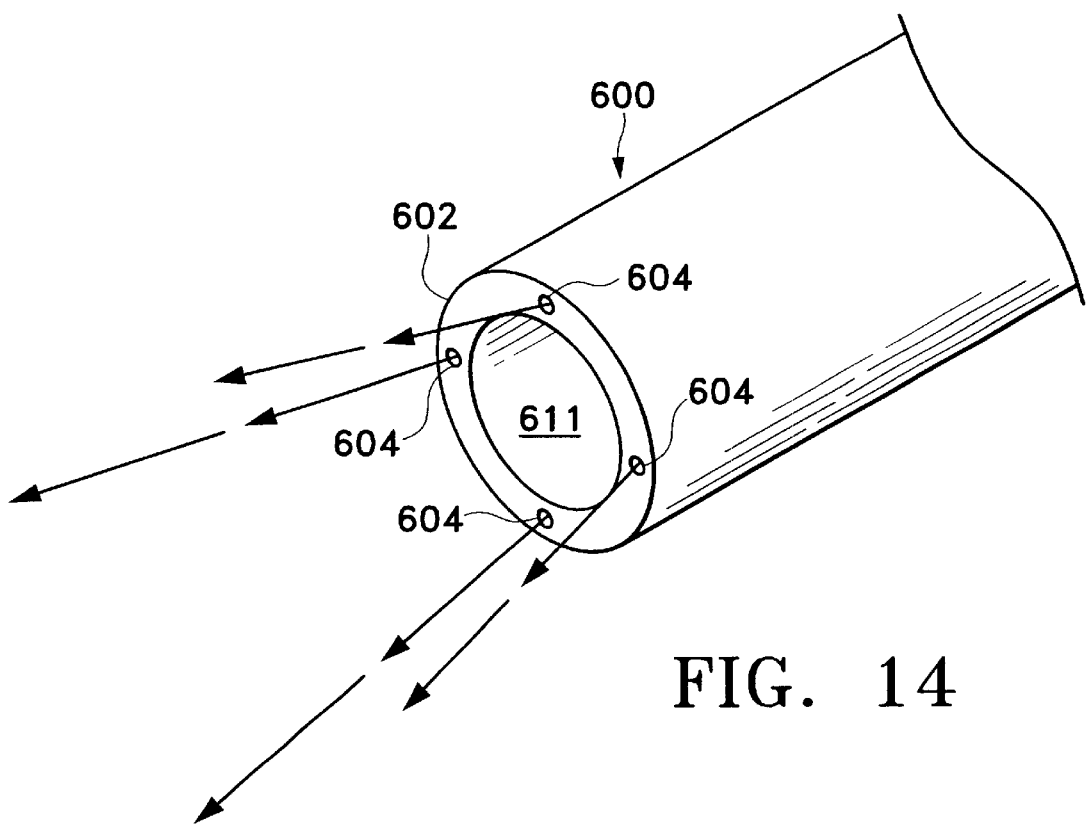
FIG. 14 is a front perspective view of one embodiment of a distal tip that may be used with the handpiece of the present invention.
Figure 15:
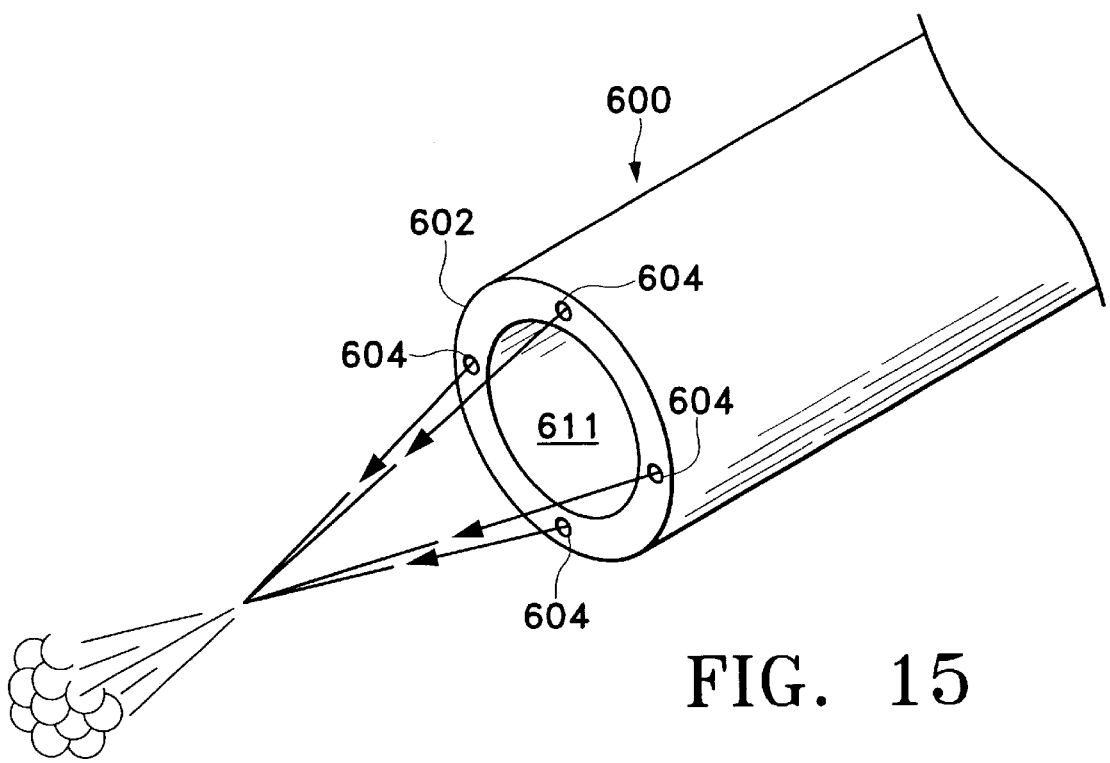
FIG. 15 is a front perspective view of a second embodiment of a distal tip that may be used with the handpiece of the present invention.
Figure 16:
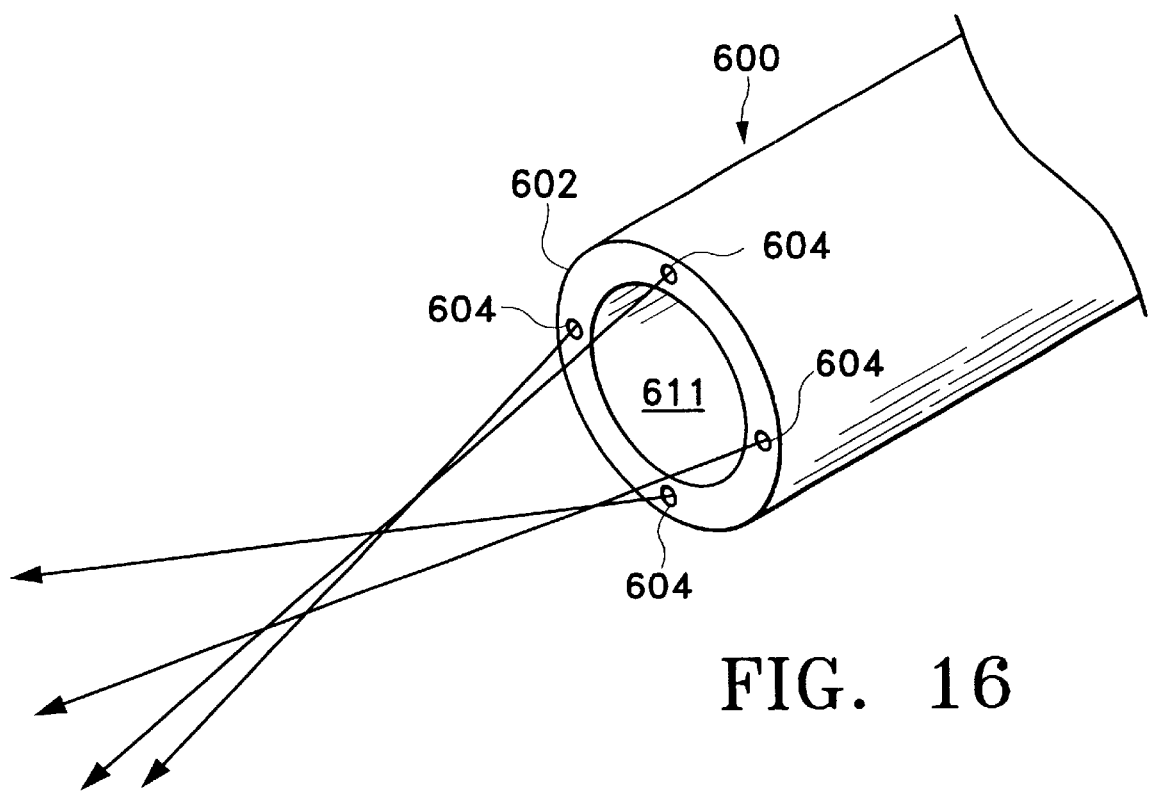
FIG. 16 is a front perspective view of a third embodiment of a distal tip that may be used with the handpiece of the present invention.
Figure 17:
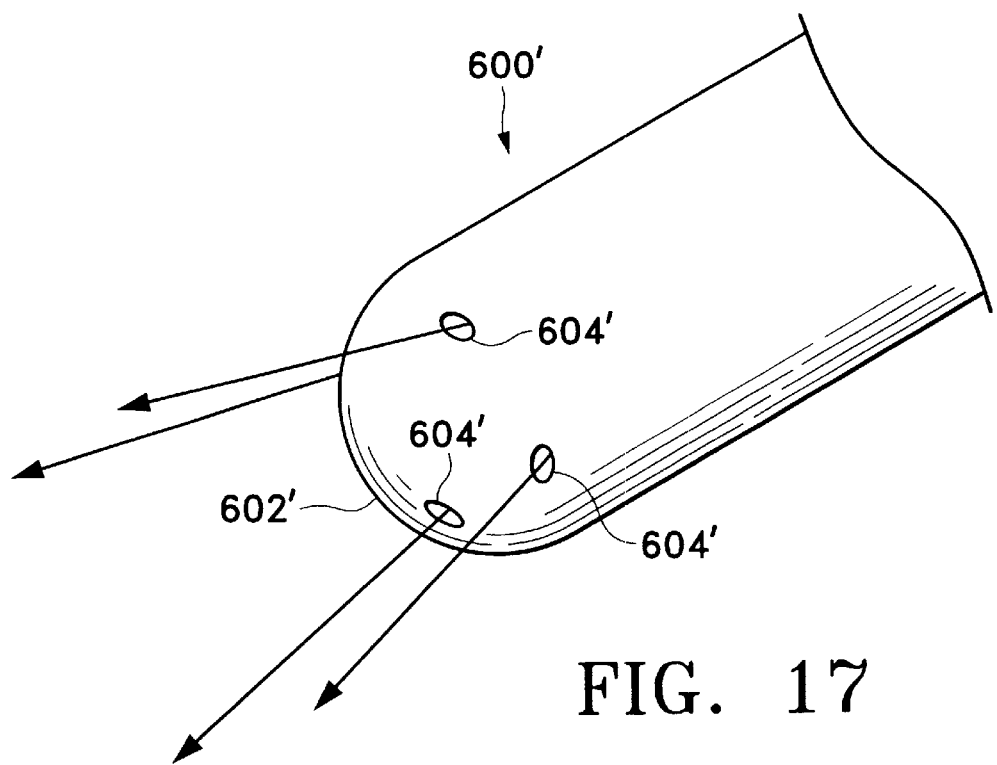
FIG. 17 is a front perspective view of a fourth embodiment of a distal tip that may be used with the handpiece of the present invention.
Figure 18:
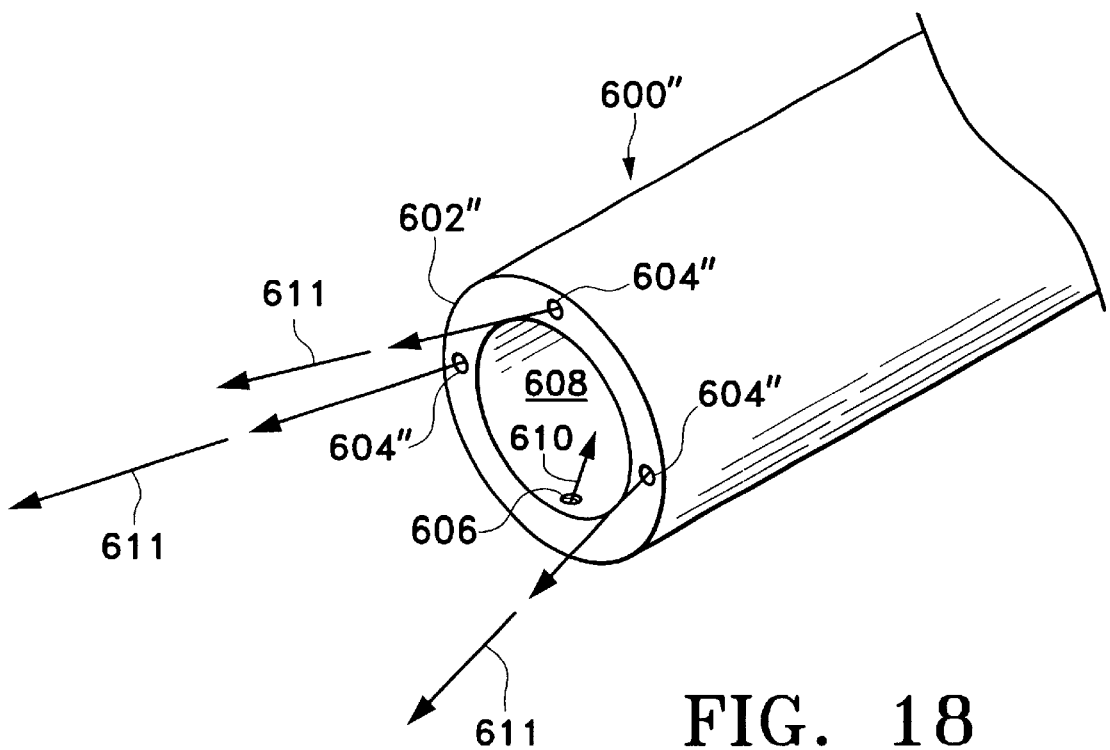
FIG. 18 is a front perspective view of a fifth embodiment of a distal tip that may be used with the handpiece of the present invention.
Figure 19:
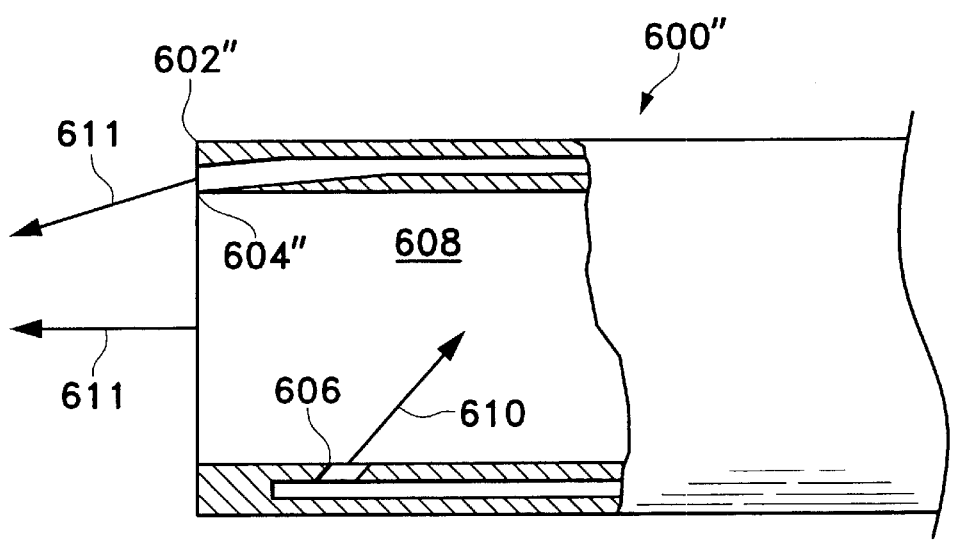
FIG. 19 is a longitudinal cross-sectional view of the tip illustrated in FIG. 18.

As best seen in FIGS. 14–21, a variety of different distal tips may be used with the handpiece of the present invention. For example, as illustrated in FIGS. 14–16, tip 600 may contain distal end 602 having a plurality of discharge orifices 604. Orifices 604 may be arranged in a divergent pattern, as illustrated in FIG. 14, a convergent pattern, as illustrated in FIG. 15, or in a non-converging, near miss pattern, as illustrated in FIG. 16, depending upon the targeted tissue and the desired surgical outcome. The converging streams create a high pressure region where the streams meet, producing a zone of maximum liquefracture. The diverging streams exhibits maximum average pressure directly in front of tip 600, making that the most efficient liquefracture zone in that region. The near miss streams create a region of high shear between the streams, which can contribute to shear fracture of the material in the proximity of tip 600. One skilled in the art will recognize that orifices 604 may be arranged so as to create the designed pattern external to tip 600 or internal to bore 611. Distal end 602 may be formed, for example by crimping the ends of tubes 165 and 167, or 265 and 267, respectively (as illustrated in FIGS. 19 and 20) so that annular gap 169 or 269 is in fluid communication with orifices 604. One skilled in the art will recognize that tip 600 may be formed as a separate piece and press fit or otherwise attached to tubes 165 and 167 or 265 and 267 so that tips 600 may be interchangeable. For example, different tip 600 designs may be desired during different portions of a surgical procedure.

Alternatively, as illustrated in FIG. 17, tip 600' may be closed on distal end 602' so that discharge orifices 604' project fluid to the targeted tissue, but tip 600' performs no aspiration function.

As seen in FIGS. 18 and 19, distal end 602" of tip 600", in addition to discharge orifices 604" projecting forward and outward discharge streams 611, may contain orifice or orifices 606 that discharge a fluid stream 610 rearward into aspiration bore 608. Stream 610 helps to assure that bore 608 does not become occluded at end 602".

Figure 21A:
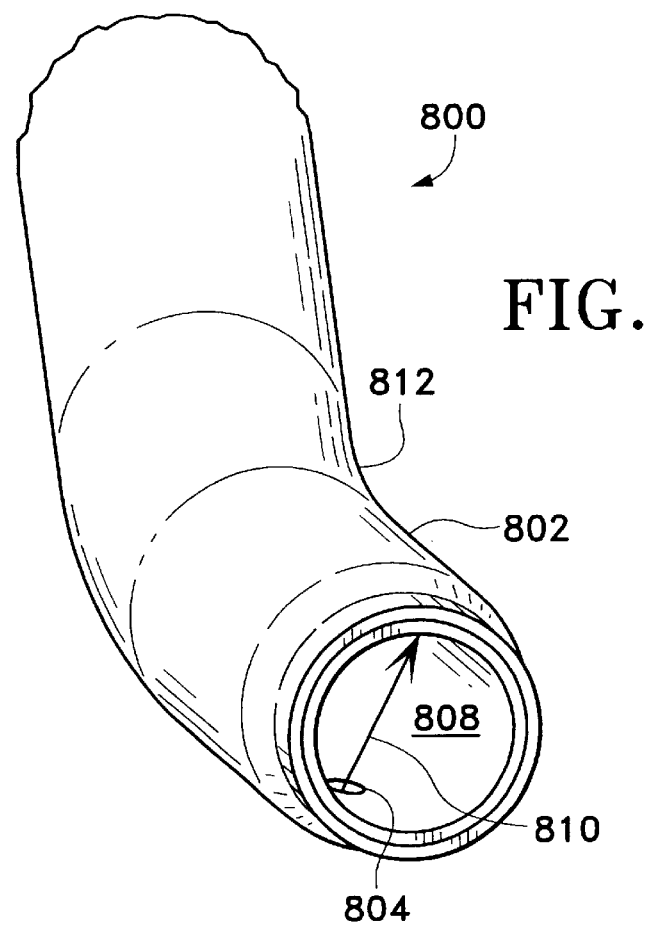
FIG. 21A is a front perspective view of a seventh embodiment of a distal tip that may be used with the handpiece of the present invention.
Figure 21B:
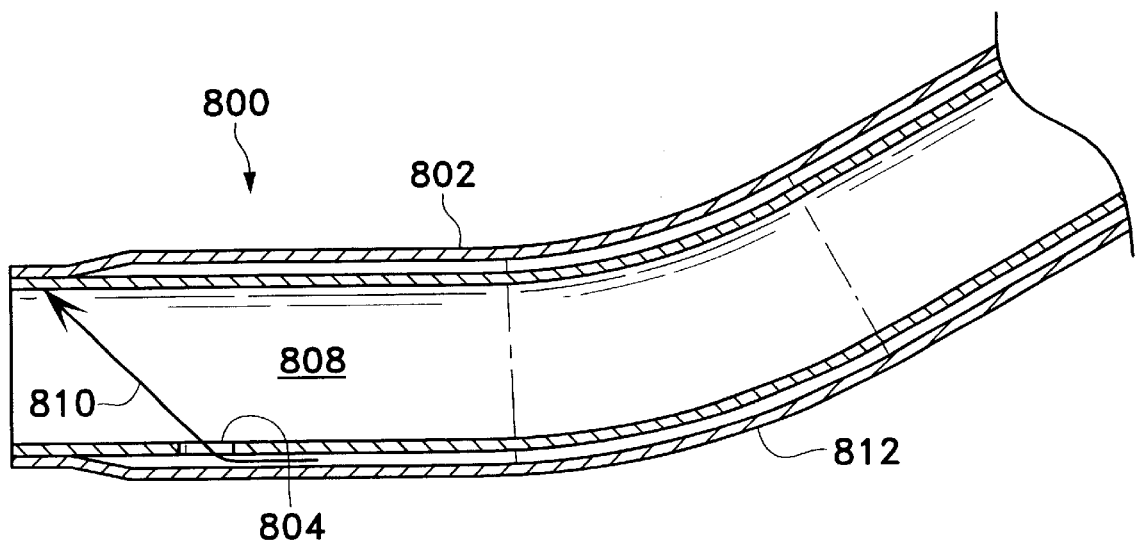
FIG. 21B is a cross sectional view of the tip illustrated in FIG. 21A.

As best seen in FIGS. 21A and 21B, distal end 802 of tip 800 may contain bend 812, bend 812 being at an angle of between 0° and approximately 90° with between 0° and approximately 60° being preferred and between 0° and approximately 20° being most preferred. Such a bend in distal end 802 allows tip 800 to access different areas within the capsular bag more easily. As discussed above, orifice 804 may be arranged to direct stream 810 internal to bore 808.

While several embodiments of the handpiece of the present invention are disclosed any handpiece producing adequate pressure pulse force, temperature, rise time and frequency may also be used. For example, any handpiece producing a pressure pulse force of between 0.02 grams and 20.0 grams, with a rise time of between 1 gram/second and 20,000 grams/second and a frequency of between 1 Hz and 200 Hz may be used, with between 10 Hz and 100 Hz being most preferred. The pressure pulse force and frequency will vary with the hardness of the material being removed. For example, the inventors have found that a lower frequency with a higher pulse force is most efficient at debulking and removing the relatively hard nuclear material, with a higher frequency and lower pulse force being useful in removing softer epinuclear and cortical material. Infusion pressure, aspiration flow rate and vacuum limit are similar to current phacoemulsification techniques.

Figure 20A:
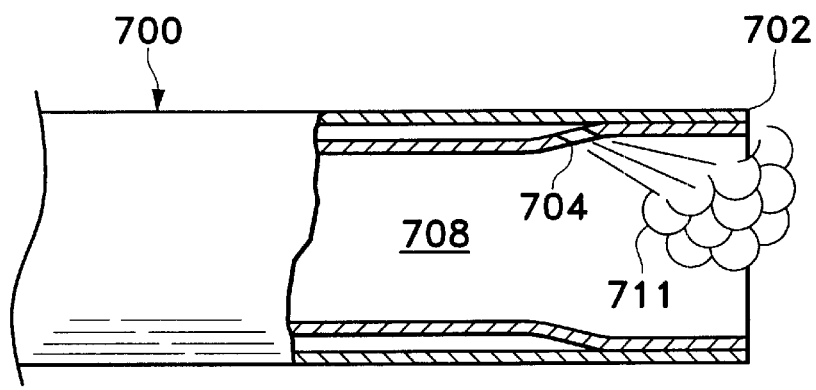
FIG. 20A is a front perspective view of a sixth embodiment of a distal tip that may be used with the handpiece of the present invention operating at high pressure with a short coherence length.
Figure 20B:
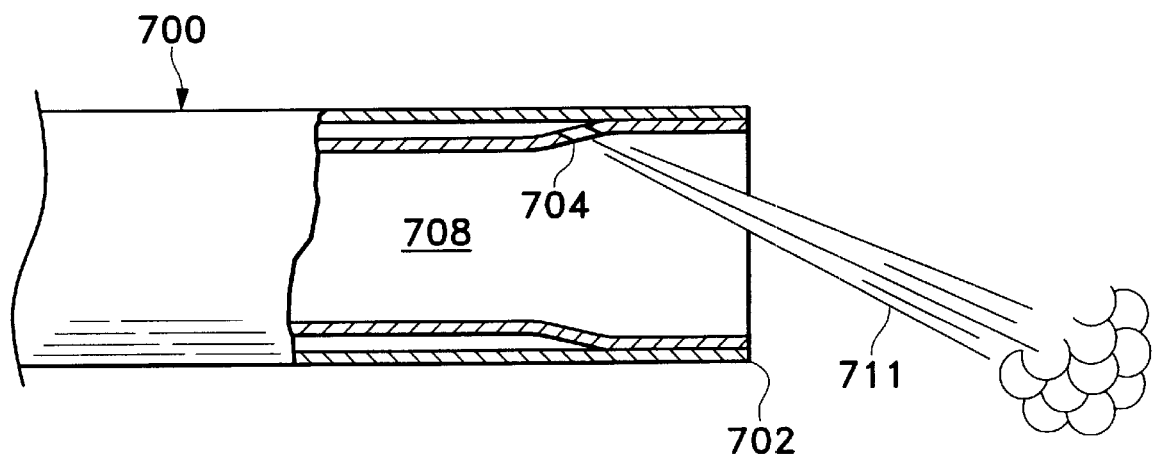
FIG. 20B is a front perspective view of a sixth embodiment of a distal tip that may be used with the handpiece of the present invention operating at low pressure with a long coherence length.

As seen in FIGS. 20A and 20B, the inventors have determined that the coherence length of the fluid stream is affected by many factors, including the properties of the fluid, ambient conditions, orifice geometry, flow regime at the orifice and pressure of the fluid. By varying the operating parameters of the system (e.g., pressure, temperature, flow development), the coherence length of the fluid pulse stream can be varied. Tip 700 contains orifice 704 internal to bore 708. When operated at relatively high pressures, as shown in FIG. 20A, the coherence length of discharge stream 711 is relatively short, degrading internal to bore 708 around distal end 702. As seen in FIG. 20B, when operated at relatively low pressures, the coherence length of discharge stream 711 is relatively long, degrading external to bore 708, past distal end 702. For example, a pressure stream having a coherence length of approximately between −1.0 millimeters and +5.0 millimeters from distal end 702 is suitable for use in ophthalmic surgery.

Figure 22:
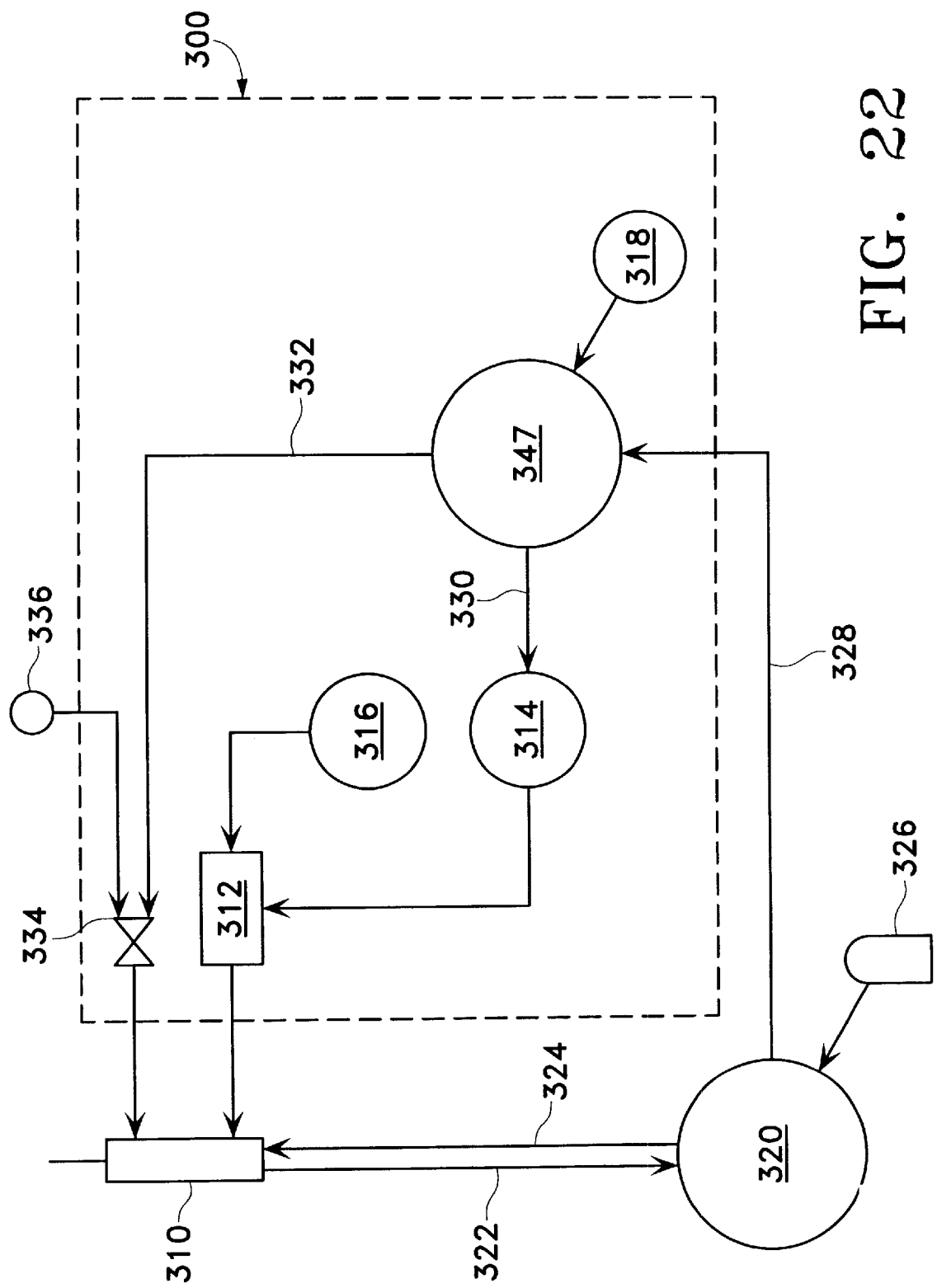
FIG. 22 is a block diagram of a control system that can be used with the handpiece of the present invention.

As seen in FIG. 22, one embodiment of control system 300 for use in operating handpiece 310 includes control module 347, power gain RF amplifier 312 and function generator 314. Power is supplied to RF amplifier 312 by DC power supply 316, which preferably is an isolated DC power supply operating at several hundred volts, but typically +200 volts. Control module 347 may be any suitable microprocessor, micro controller, computer or digital logic controller and may receive input from operator input device 318. Function generator 314 provides the electric wave form in kilohertz to amplifier 312 and typically operates at around 450 kHz or above to help minimize corrosion.

In use, control module 347 receives input from surgical console 320. Console 320 may be any commercially available surgical control console such as the LEGACY® SERIES TWENTY THOUSAND® surgical system available from Alcon Laboratories, Inc., Fort Worth, Tex. Console 320 is connected to handpiece 310 through irrigation line 322 and aspiration line 324, and the flow through lines 322 and 324 is controlled by the user via footswitch 326. Irrigation and aspiration flow rate information in handpiece 310 is provided to control module 347 by console 320 via interface 328, which may be connected to the ultrasound handpiece control port on console 320 or to any other output port. Control module 347 uses footswitch 326 information provided by console 320 and operator input from input device 318 to generate two control signals 330 and 332. Signal 332 is used to operate pinch valve 334, which controls the surgical fluid flowing from fluid source 336 to handpiece 310. Fluid from fluid source 336 is heated in the manner described herein. Signal 330 is used to control function generator 314. Based on signal 330, function generator 314 provides a wave form at the operator selected frequency and amplitude determined by the position of footswitch 326 to RF amplifier 312 which is amplified to advance the powered wave form output to handpiece 310 to create heated, pressurized pulses of surgical fluid.

Any of a number of methods can be employed to limit the amount of heat introduced into the eye. For example, the pulse train duty cycle of the heated solution can be varied as a function of the pulse frequency so that the total amount of heated solution introduced into the eye does not vary with the pulse frequency. Alternatively, the aspiration flow rate can be varied as a function of pulse frequency so that as pulse frequency increases aspiration flow rate increases proportionally.

This description is given for purposes of illustration and explanation. It will be apparent to those skilled in the relevant art that changes and modifications may be made to the invention described above without departing from its scope or spirit. For example, it will be recognized by those skilled in the art that the present invention may be combined with ultrasonic and/or rotating cutting tips to enhance performance.

We claim:

1. A tip for a liquefracture handpiece, comprising:

a) an inner aspiration tube coaxially mounted within an outer tube so as to form an annular gap between the inner tube and the outer tube, the annular gap being fluidly connected to a boiling chamber;

b) distal ends on the inner tube and the outer tube, the distal ends each containing a bend and sealing the annular gap; and c) at least one discharge orifice in the distal end of the inner tube, the orifice in fluid communication with the annular gap.

2. The tip of claim 1 wherein the bend is at an angle of between 0° and approximately 90°.

3. The tip of claim 1 wherein the bend is at an angle of between 0° and approximately 60°.

4. The tip of claim 1 wherein the bend is at an angle of between 0° and approximately 20°.

* * * * *